US00PP17624P3

(12) United States Plant Patent
Hart

(10) Patent No.: US PP17,624 P3
(45) Date of Patent: Apr. 17, 2007

(54) PEAR TREE NAMED 'PREM1P'

(50) Latin Name: ***Pyrus communis*×*Pyrus pyrifolia***
Varietal Denomination: Prem1P

(75) Inventor: Roy Hart, Nelson (NZ)

(73) Assignee: Prevar Limited, Hastings (NZ)

( * ) Notice: Subject to any disclaimer, the term of this patent is extended or adjusted under 35 U.S.C. 154(b) by 0 days.

(21) Appl. No.: 10/900,691

(22) Filed: Jul. 27, 2004

(65) Prior Publication Data

US 2006/0026724 P1 Feb. 2, 2006

(51) Int. Cl.
*A01H 5/00* (2006.01)

(52) U.S. Cl. ..... Plt./176
(58) Field of Classification Search ..... Plt./176
See application file for complete search history.

(56) References Cited

PUBLICATIONS

UPOV ROM GTITM Computer Database, GTI Jouve Retrieval Software 2005/03 Citation for 'Maxie'.*
*New Zealand Plant Variety Rights Journal*, No. 75, Jul.–Sep. 1998, published Oct. 14, 1998, p. 2.
Application for Plant Variety Rights under Plant Variety Right Act 1987 (New Zealand), filed Jul. 2, 1998.

* cited by examiner

*Primary Examiner*—Anne Marie Grunberg
*Assistant Examiner*—S. B. McCormick-Ewoldt
(74) *Attorney, Agent, or Firm*—Stratton Ballew PLLC

(57) ABSTRACT

A new distinct pear variety is described. This interspecific variety results from crossing varieties, 'Nijisseiki' (*Pyrus pyrifolia* Nakai) (not patented) and 'Max Red Bartlett' (*Pyrus communis*) (U.S. Plant Pat. No. 741). The new variety has been named 'Prem1P' and was selected because of its crisp texture and strong 'Barlett' type flavor. The fruit of this new variety is characterized by its round to high round fruit shape which has 50–70% red blush coverage.

7 Drawing Sheets

Genus and species of plant claimed: *Pyrus communis*× *Pyrus pyrifolia.*
Variety denomination: 'Prem1P'.

BACKGROUND OF THE INVENTION

A new distinct pear variety is described. This interspecific variety originated as a single plant resulting from crossing varieties 'Nijisseiki' (*Pyrus pyrifolia* Nakai) (not patented) and 'Max Red Bartlett' (*Pyrus communis*) (U.S. Plant Pat. No. 741). The new variety has been named 'Prem1P' and was selected because of its crisp texture and strong 'Bartlett' type flavour. The fruit of this new variety is characterised by its round to high round fruit shape which has 50–70% red blush coverage.

SUMMARY OF INVENTION

This new variety was selected from a population of seedlings derived from crossing the pear varieties 'Nijisseiki' and 'Max Red Bartlett'. The cross was made in 1987 at Motueka, Nelson, New Zealand. The variety was determined to be distinct from the parent varieties by the following characteristics:

Nijisseiki: 'Prem1P' fruit has 50–70 percent red colour while 'Nijisseiki' has none; strong 'Bartlett' like flavour when fully ripe compared with the delicate flavour of 'Nijisseiki'; a layer of stone cells around the core while 'Nijisseiki' has none.

'Max Red Bartlett': 'Prem1P' had a round to high round shape compared to the pyriform shape of 'Max Red Bartlett'; 'Prem1P' has red skin colour and can have a 'speckled' appearance where colour is concentrated around lenticels while the colour on 'Max Red Bartlett' has fuller skin coverage.

'Williams Bon Chretien': 'Prem1P' has a round to high round shape compared to the pyriform shape of 'Williams Bon Chretien'; 'Prem1P's' red skin colour and can have a 'speckled' appearance where colour is concentrated around lenticels while 'Williams Bon Chretien' has no skin colour.

True to type budding and grafting onto Quince rootstock 'BA29' with 'Buerre Hardy' pear as an interstock has been used to obtain plants. Asexual propagation by budding and grafting has shown that the unique combination of characteristics of the variety is consistently transferred through successive propagation.

BRIEF DESCRIPTION OF THE DRAWING

The accompanying photographs show typical specimens of the tree, foliage, fruit of the new variety, identified as "Maxie", as depicted in colours as nearly true as is reasonably possible in a colour illustration of this character.

MORPHOLOGICAL DESCRIPTION OF THE VARIETY

Figure 1:
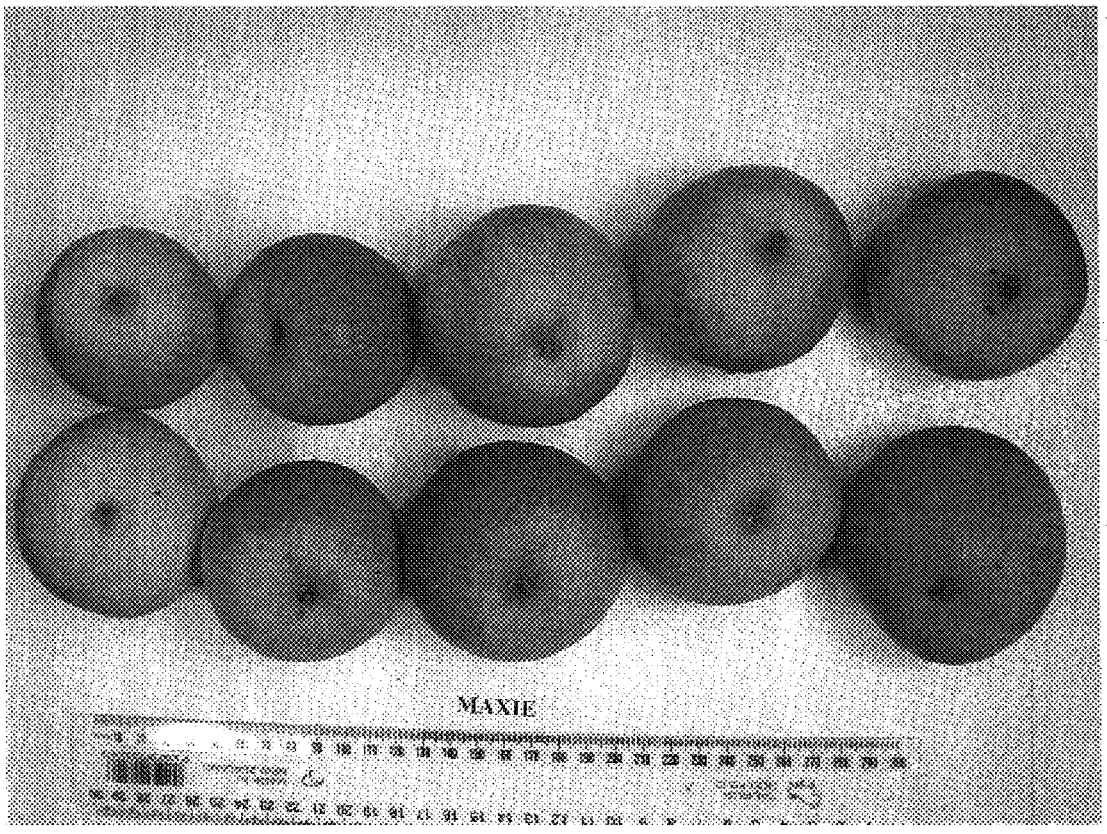
FIG. 1: calyx end view of typical fruit of the pear variety 'Prem1P'.
Figure 2:
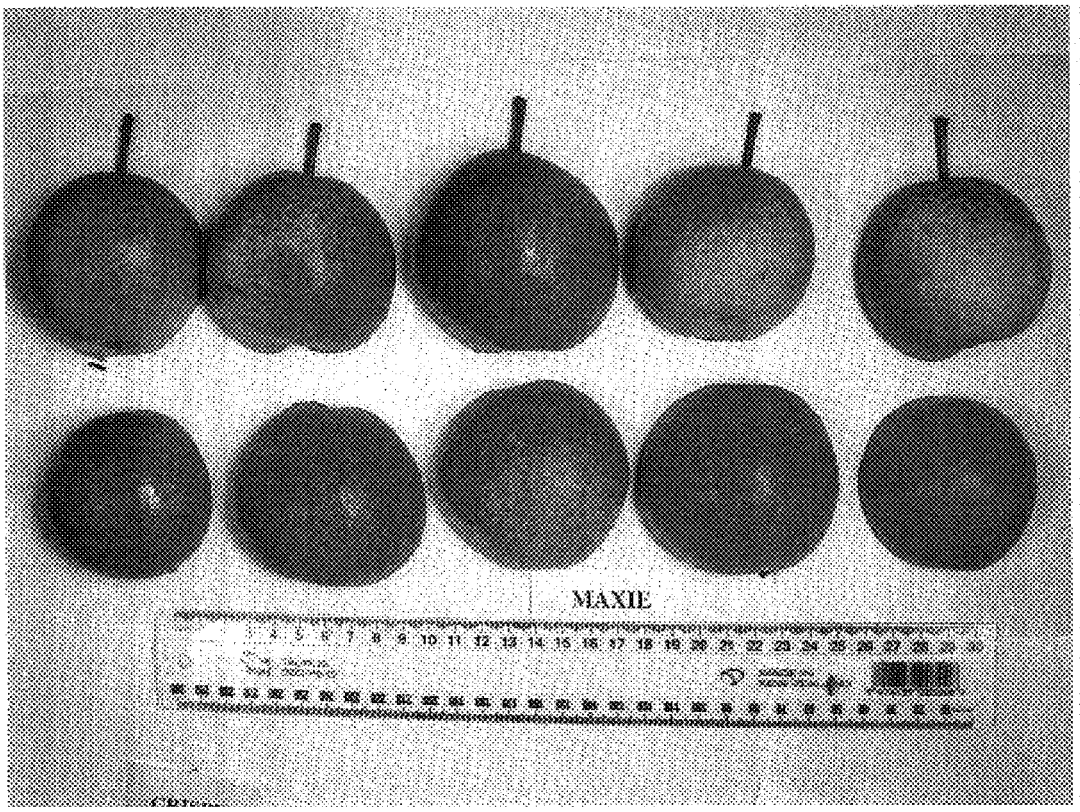
FIG. 2: side view of typical fruit of the pear variety 'Prem1P'.
Figure 3:
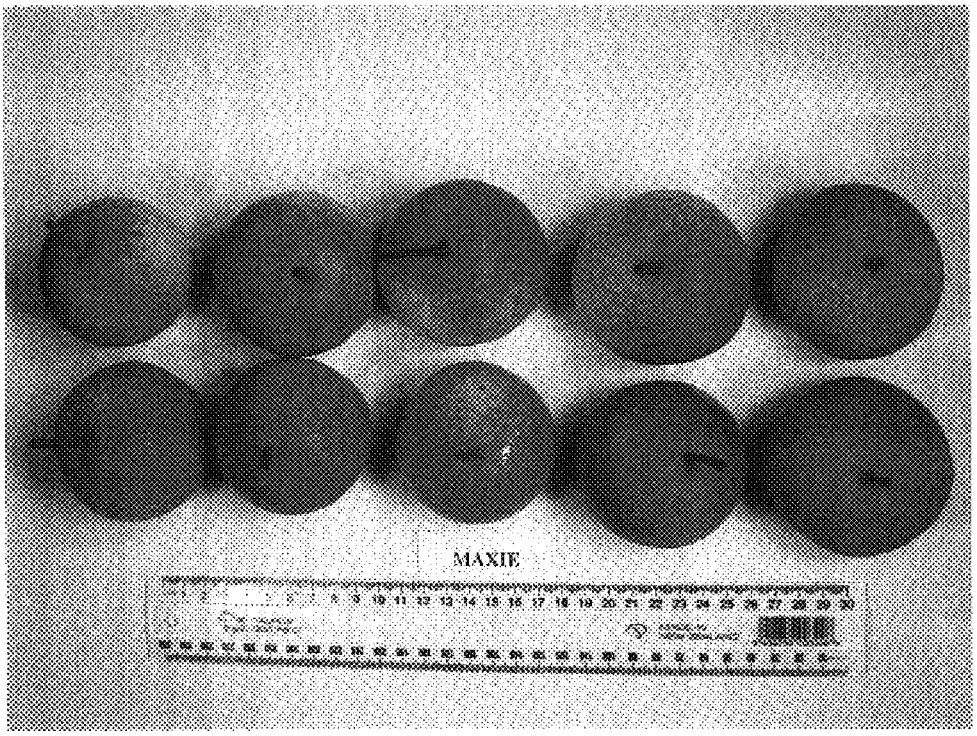
FIG. 3: stem end view of a typical fruit of the pear variety 'Prem1P'.
Figure 4:
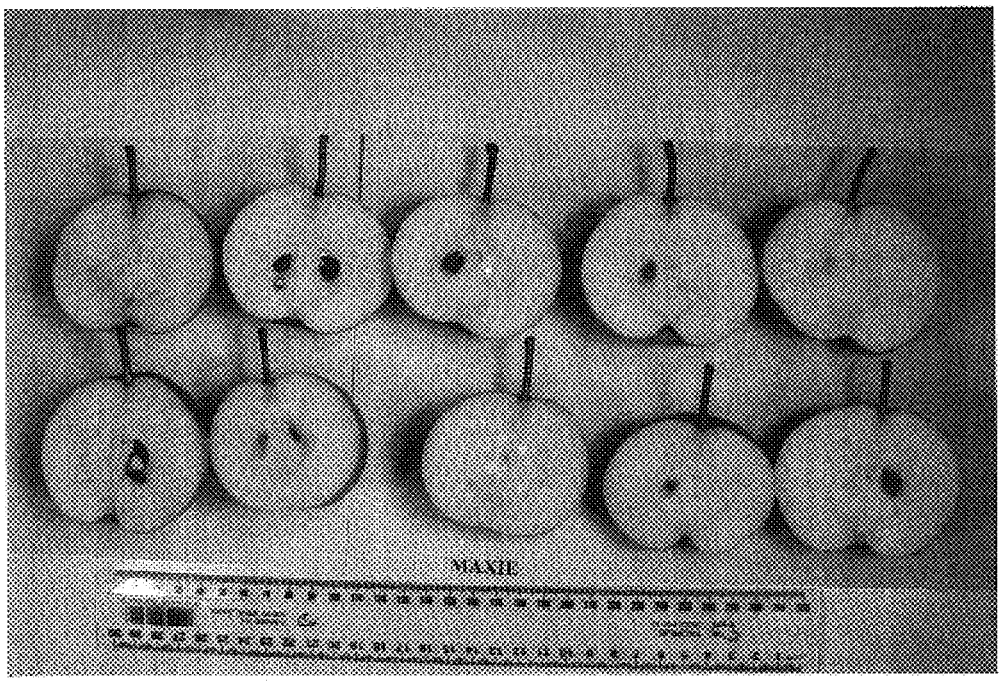
FIG. 4: cross sectional view of a typical fruit of the pear variety 'Prem1P'.
Figure 5:
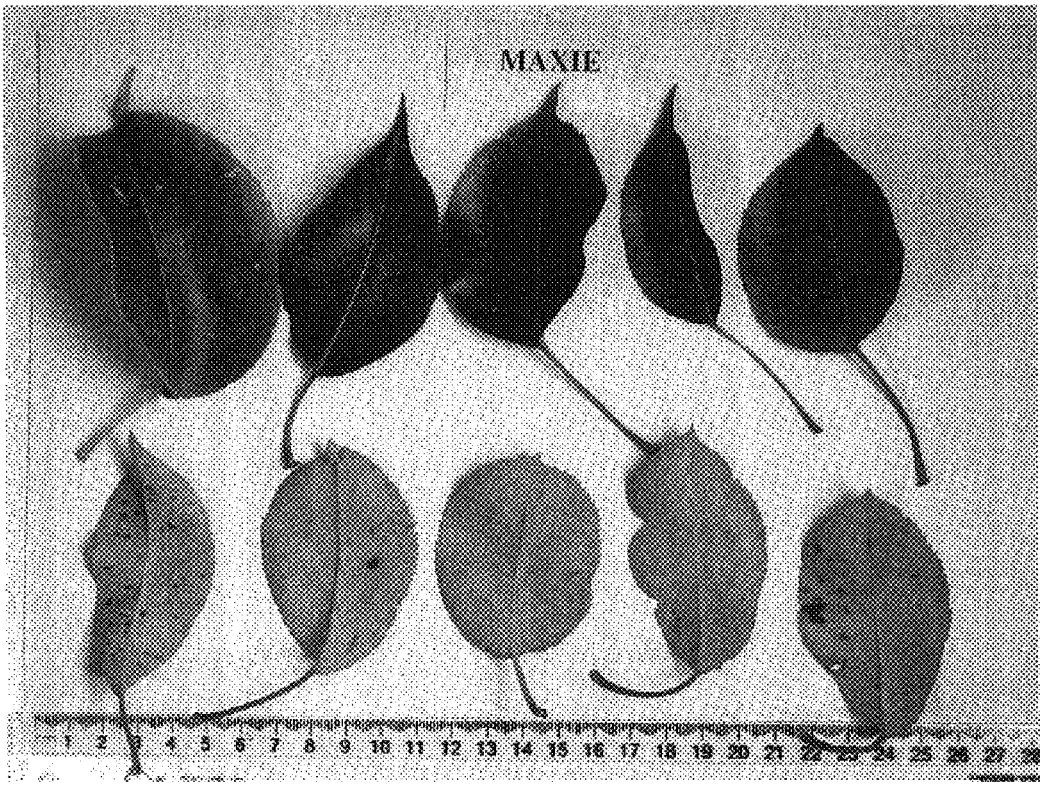
FIG. 5: typical mature leaves of 'Prem1P' showing the upper and lower surfaces.
Figure 6:
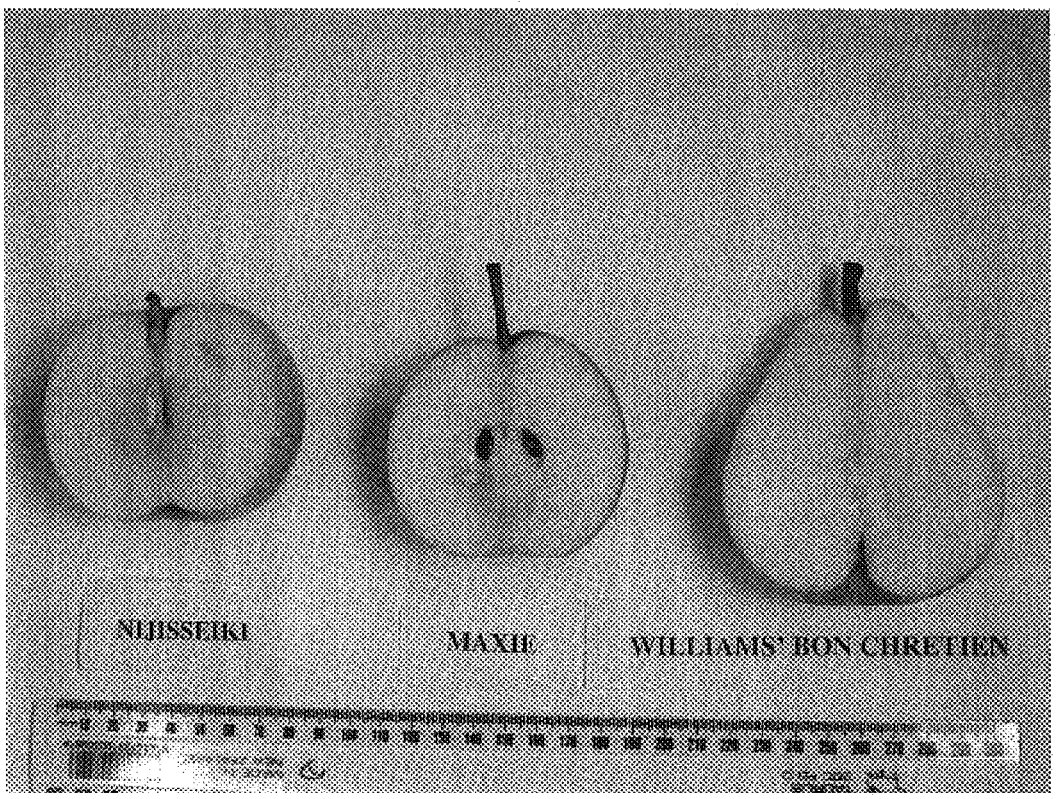
FIG. 6: cross sectional fruit view of 'Nijisseiki', (far left), 'Prem1P' (middle), 'Williams Bon Chretien' (right).
Figure 7:
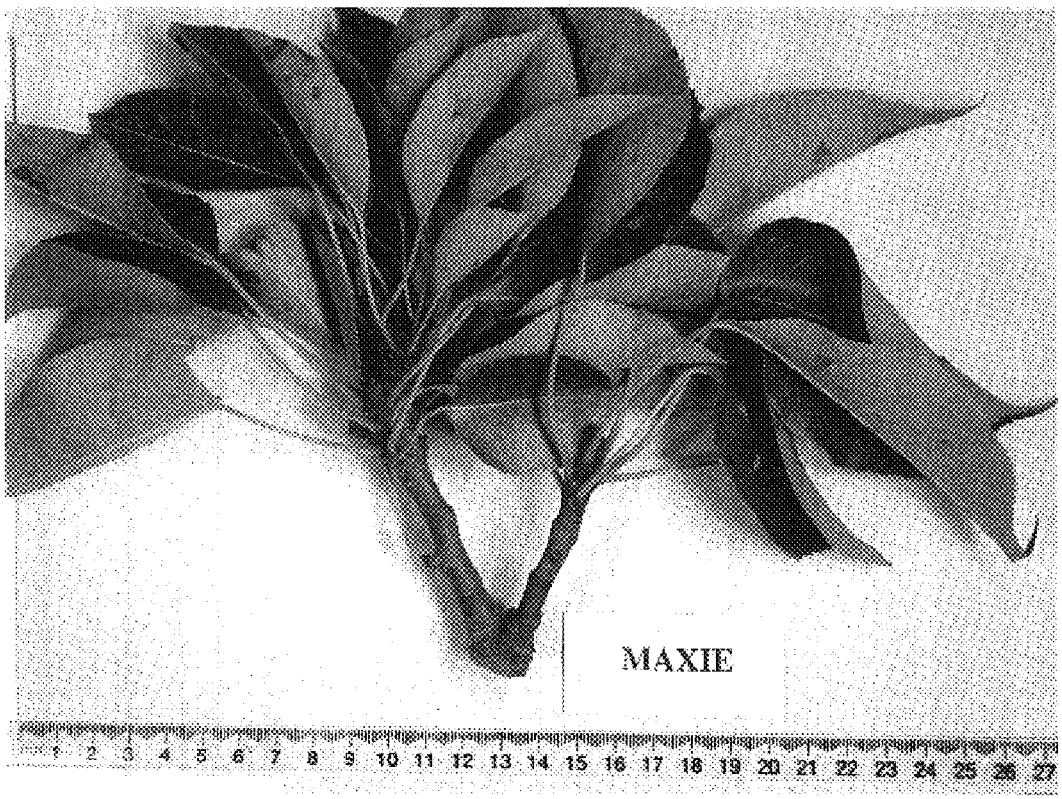
FIG. 7: fruiting spur 'Prem1P'.

The following is a detailed description of the new variety with colour terminology in accordance with The Royal Horticultural Society Colour charts (R.H.S.C.C.) 2001 edition.

The observations were made in the 2003–2004 season on four year old trees grafted onto Quince 'BA29' rootstocks with a 'Buerre Hardy' pear interstock and planted in the orchard in 1999. The observations were made at Motueka, New Zealand. In this growing location, the climate is temperate, with 2418 sunshine hours; humidity between 65% and 85%; moderately high rainfall at 1381 mm per year; and moderate temperatures, average daily maximum 18° C., minimum 6.9° C.

Tree: Vigour when grafted onto Quince 'BA29' rootstocks with a 'Buerre Hardy' interstock weak; size medium small; semi upright; branching weak; bearing on spurs which can become multi spurred.

Trunk: Bark is grey R.H.S.C.C. N200D when mature; trunk circumference of 162 mm at the height of 200 mm; texture of bark smooth with few cracks; lenticels 4.8 per 10 $mm^2$, length 5.27 mm, width 2.87 mm; lenticel color greyed yellow R.H.S.C.C. 198C.

Branches: Thin; weak, little branching, approximately 4 spurs/100 mm of 2 year old wood; low annual growth numbers with a length of 400–500 mm; annual growth wood brown purple R.H.S.C.C. N77A; lower branch diameter 33.6 mm, upper branch diameter 24.9 mm; average crotch angle 40.1 degrees, ranging from 21 degrees to 80 degrees.

Branch lenticels: Medium numbers of large sized lenticels on current year's growth; average 4.2 per 10 $mm^2$; length 1.89 mm, width 2.06 mm; color greyed yellow R.H.S.C.C. 162C.

Leaves: Average length 60 mm; width 48 mm; length/width ratio 1.24; downward pose, upfolded shape in cross section; indentations of the margin bluntly serrate, medium depth; shape of leaf blade oval, shape of leaf blade base obtuse, shape of leaf blade apex obtuse, shape of leaf blade tip pointed, 9.75 mm tip; petiole length 36 mm–51 mm; stipules absent; colour of leaf blade upper surface green R.H.S.C.C. 146A; colour of leaf blade lower surface R.H.S.C.C. 137C.

Flower buds: Flower bud length medium short; stigma can protrude above flower bud petals.

Flowers: Bloom period medium-late, starting September 25 until October 15 in Nelson New Zealand, full bloom date October 4: sepal length medium, sepal attitude in relation to the corolla spreading; average sepal length 4.57 mm, width 3.11 mm; sepal shape rectangular with obtuse tip; sepal margin smooth, slightly indented to the middle sepal color upper surface R.H.S.C.C. orange 29D, lower surface R.H.S.C.C. greyed orange 166D; margins of petals overlapping; position of stigma in relation to stamens above; petal length 13.2 mm; petal width 13.1 mm; shape of petal (excluding claw) circular; shape of petal base (excluding claw) cordate; length of claw petal short; flower diameter 25.5 mm.

Reproductive organs: Average stamen quantity 22.2, pollen amount high, pollen color R.H.S.C.C. yellow 2D.

Fruit: Fruit is mature for consumption in early March; harvest period is from February 20 to March 5 in Nelson New Zealand.

Fruit size: Medium small; average fruit weight 160 g; average width 72 mm; average height 66 mm; fruit length/diameter ratio small; maximum diameter in middle of fruit.

Stalk cavity: Shallow, average 4 mm.

Shape: Round — high round; slightly asymmetric in longitudinal section; profile of the sides convex.

Eye basin: Average width 26 mm; average depth 7 mm, relative area of russet around eye basin absent or very small.

Stalk: Diameter thick, 3.79 mm, length medium, average 26 mm; stalk color R.H.S.C.C. greyed orange 165B, sunny side R.H.S.C.C. greyed orange 172B; curvature of stalk absent or very weak, attitude of the stalk is straight in relation to the axis of the fruit.

Sepal: Calyx or sepals are partially persistent, approximately 40% of fruit at harvest have a deciduous calyx and sepals, remaining 60% have erect to spreading sepals.

Skin: Smooth; greasiness absent, cracking tendency of skin absent; thick; background colour, yellow R.H.S.C.C. 7D; lenticels medium.

Overcolour: 50–70% of skin surface red R.H.S.C.C. 46A, amount of russet around the stem cavity absent to low.

Flesh color: White.

Texture: Crisp, flesh medium; firmness penetrometer measurements taken at harvest on Mar. 4, 2003 were 6.5 kg; flesh juicy; medium numbers of large stone cells around the core cavity.

Flavour: Sweetness medium, degrees Brix 11.3; acidity low, titratable acids 0.21% strong 'Bartlett' like aroma when ripe.

Quality: Very good.

Seeds: Locules 5, seeds per locule 1–2; medium seed size 11 mm long, 5 mm wide; colour, black R.H.S.C.C. 202A.

Use: Dessert.

Production: Mid season, regular cropping when thinned.

Temperature tolerances: High and low temperature tolerance unknown; tree is expected to perform well in areas where *Pyrus pyrifolia* and *Pyrus communis* are successfully grown.

Management: Thinning of crop load in early summer is recommended. Minimal pruning is required because spur bearing habit and the limited amount of one year wood produced.

Pest and disease: Susceptible to pear slug (*Caliroa cerasi*); highly leaf and fruit resistant to pear scab (*Venturia pirina* Adherh).

Keeping and shipping quality: Cool storage testing on fruit harvested at Nelson, New Zealand on Mar. 4, 2003 and stored for 4 weeks at 0.5° C. followed by 7 days shelf life at 20° C. had flesh firmness readings of 2.9 kg, soluble solids of 11.1%, titratable acids at 0.26% and internal ethylene levels of 528 ppm. Fruit harvested on Mar. 8, 2003 and stored as above showed 5% core breakdown and 5% rots. Core breakdown becomes more significant when fruit is tree ripe before storage.

I claim:

1. A new and distinct variety of pear tree named 'Prem1P' substantially as herein illustrated and described.

* * * * *

UNITED STATES PATENT AND TRADEMARK OFFICE

CERTIFICATE OF CORRECTION

PATENT NO. : PP 17,624 P3
APPLICATION NO. : 10/900691
DATED : April 17, 2007
INVENTOR(S) : Roy Hart It is certified that error appears in the above-identified patent and that said Letters Patent is hereby corrected as shown below:

TITLE PAGE
In the Title Item (54), replace "PREM1P" with --PREMP45--
Item (50) in the Varietal Denomination, replace "Prem1P" with --PremP45--
Item (57) in the Abstract, replace "Prem1P" with --PremP45--
At column 1, lines 5, 24, 29 and 31 replace "Prem1P" with --PremP45--
At column 2, lines 1, 3, 21, 23, 25, 27, 29, 33 and 35 replace "Prem1P" with --PremP45--
In the Claim, replace "Prem1P" with --PremP45--

Signed and Sealed this

First Day of September, 2009

David J. Kappos

David J. Kappos
*Director of the United States Patent and Trademark Office*